(12) United States Patent
Parker

(10) Patent No.: US 10,595,971 B2
(45) Date of Patent: Mar. 24, 2020

(54) ORTHODONTIC SYSTEM ANCHORING METHOD AND APPARATUS

(71) Applicant: Justin Parker, Salt Lake City, UT (US)

(72) Inventor: Justin Parker, Salt Lake City, UT (US)

( * ) Notice: Subject to any disclaimer, the term of this patent is extended or adjusted under 35 U.S.C. 154(b) by 88 days.

(21) Appl. No.: 14/684,351

(22) Filed: Apr. 11, 2015

(65) Prior Publication Data

US 2016/0296303 A1    Oct. 13, 2016

Related U.S. Application Data

(63) Continuation-in-part of application No. 13/478,722, filed on May 23, 2012, now Pat. No. 8,610,829.

(51) Int. Cl.
| | |
|---|---|
| *A61C 8/00* | (2006.01) |
| *A61C 7/06* | (2006.01) |
| *A61C 7/08* | (2006.01) |
| *A61C 7/30* | (2006.01) |
| *A61C 7/28* | (2006.01) |
| *A61N 1/05* | (2006.01) |
| *A61C 7/10* | (2006.01) |
| *A61C 7/00* | (2006.01) |

(52) U.S. Cl.
CPC .............. *A61C 8/0096* (2013.01); *A61C 7/06* (2013.01); *A61C 7/08* (2013.01); *A61C 7/10* (2013.01); *A61C 7/282* (2013.01); *A61C 7/303* (2013.01); *A61N 1/0548* (2013.01); *A61C 7/006* (2013.01); *A61C 7/008* (2013.01)

(58) Field of Classification Search
CPC ........... A61C 8/0096; A61C 7/06; A61C 7/10; A61C 7/282; A61C 7/08; A61C 7/303; A61C 7/008; A61C 7/006; A61N 1/0548

USPC ....................................................... 433/7–24
See application file for complete search history.

(56) References Cited

U.S. PATENT DOCUMENTS

| | | | |
|---|---|---|---|
| 1,292,702 | A | 1/1919 | Canning |
| 1,487,698 | A | 7/1921 | Adero |
| 1,481,861 | A | 4/1922 | Eaton |
| 1,764,067 | A | 3/1928 | Craigo |
| 3,855,701 | A | 12/1974 | Le Clair |

(Continued)

OTHER PUBLICATIONS en.wikipedia.org/wiki/Dental_braces, Jun. 4, 2012.
en.wikipedia.or/wiki/Occlusion_(dentisry), Jun. 4, 2012.

*Primary Examiner* — Matthew M Nelson
(74) *Attorney, Agent, or Firm* — Marcus G. Theodore

(57) ABSTRACT

Orthodontic system anchoring method and custom apparatus affixed to teeth, TADs and/or tooth positioning and stabilization appliances and/or orthodontic auxiliaries. Each appliance has mechanical fasteners structured to secure segments of a curable flexible resin rope called a flex fit module (FFM). The FFM is moldable and adaptable to the oral cavity between mechanical fasteners in an uncured first mode where it is cut to length, positioned around the anatomy of the mouth and attached to clamps or fasteners at each end. Each fastener has a clamp attached to orthodontic auxiliaries, orthodontic appliances or onto a TAD for anchorage purposes. One end of this custom appliance is usually attached via a clamp manufactured as part of a bracket or band to a tooth. The other end is connected to an appliance, tad or auxiliary. Once connected together the system is cured and becomes a solid entity ready to accept orthodontic forces.

4 Claims, 19 Drawing Sheets
(4 of 19 Drawing Sheet(s) Filed in Color)

(56) References Cited

U.S. PATENT DOCUMENTS

| | | |
|---|---|---|
| 4,292,025 A | 9/1981 | Forster |
| 4,371,337 A | 2/1983 | Pletcher |
| 4,419,078 A | 12/1983 | Pletcher |
| 4,468,196 A | 8/1984 | Keller |
| 4,472,138 A * | 9/1984 | Howe ............... A61C 7/36 433/19 |
| 4,559,012 A | 12/1985 | Pletcher |
| 4,643,662 A | 2/1987 | Rakestraw et al. |
| 4,820,151 A | 4/1989 | Pospisil |
| 5,167,499 A | 12/1992 | Arndt et al. |
| RE35,170 E | 3/1996 | Arndt et al. |
| 5,820,369 A | 10/1998 | Kvarnstrom et al. |
| 5,869,178 A * | 2/1999 | Kusy ............... B29B 15/122 428/330 |
| 5,913,680 A | 6/1999 | Voudouris |
| 5,921,778 A | 7/1999 | Karmaker et al. |
| 5,967,772 A | 10/1999 | Gray |
| 6,030,220 A | 2/2000 | Karmaker et al. |
| 6,132,215 A * | 10/2000 | Prasad ............... A61C 5/007 433/180 |
| 6,186,790 B1 | 2/2001 | Karmaker et al. |
| 6,345,984 B2 | 2/2002 | Karmaker et al. |
| 6,362,250 B1 | 3/2002 | Karmaker et al. |
| 6,381,989 B1 | 5/2002 | Karmaker et al. |
| 6,413,082 B2 | 7/2002 | Binder |
| 6,485,299 B1 | 11/2002 | Wildman |
| 6,568,935 B2 | 5/2003 | Clark |
| 6,599,125 B1 * | 7/2003 | Freilich ............... A61C 5/007 433/180 |
| 6,726,474 B2 | 4/2004 | Spencer |
| 6,863,528 B2 | 3/2005 | Lin |
| 6,964,565 B2 | 11/2005 | Abels et al. |
| 7,011,518 B2 | 3/2006 | DeLuke |
| 7,018,202 B2 | 3/2006 | Teramoto |
| 7,101,177 B2 | 9/2006 | Lin |
| 7,125,254 B2 | 10/2006 | Calvert |
| 7,125,750 B2 | 10/2006 | Kwan et al. |
| 7,611,352 B2 | 11/2009 | Abels et al. |
| 7,611,353 B2 | 11/2009 | Sommer |
| 7,717,707 B2 | 5/2010 | Cope |
| 7,758,785 B2 * | 7/2010 | Gopal ............... B29C 70/44 264/134 |
| 7,934,927 B2 | 5/2011 | Yazdi |
| 8,167,613 B2 | 5/2012 | Forster |
| 2001/0005575 A1 * | 6/2001 | Kanomi ............... A61C 7/00 433/18 |
| 2002/0182560 A1 | 12/2002 | Park et al. |
| 2002/0187453 A1 | 12/2002 | Clark et al. |
| 2003/0044746 A1 | 3/2003 | Marrotta et al. |
| 2003/0044754 A1 * | 3/2003 | Deslauriers ............... A61C 7/00 433/215 |
| 2003/0049581 A1 | 3/2003 | DeLuke |
| 2003/0124482 A1 | 7/2003 | Calvert |
| 2003/0207225 A1 | 11/2003 | Huge et al. |
| 2004/0214126 A1 | 10/2004 | Forster et al. |
| 2004/0241614 A1 * | 12/2004 | Goldberg ............ A61C 13/0003 433/202.1 |
| 2005/0130093 A1 | 6/2005 | Lin |
| 2005/0186525 A1 | 8/2005 | Abels et al. |
| 2005/0227197 A1 | 10/2005 | Lin |
| 2005/0277089 A1 | 12/2005 | Brajnovic |
| 2006/0078849 A1 * | 4/2006 | Parks ............... A61C 5/00 433/215 |
| 2006/0188833 A1 | 8/2006 | Carriere Lluch |
| 2006/0199138 A1 | 9/2006 | Corti et al. |
| 2006/0208393 A1 * | 9/2006 | Karmaker ............... A61K 6/083 264/230 |
| 2007/0178421 A1 | 8/2007 | McSurdy, Jr. |
| 2007/0218416 A1 | 9/2007 | Keles |
| 2007/0231766 A1 | 10/2007 | Cope |
| 2007/0231768 A1 | 10/2007 | Hutchinson |
| 2008/0057459 A1 | 3/2008 | Abels et al. |
| 2008/0241782 A1 | 10/2008 | Abels et al. |
| 2008/0254401 A1 | 10/2008 | Yazdi |
| 2009/0130620 A1 | 5/2009 | Yazdi et al. |
| 2009/0148804 A1 | 6/2009 | Marcus |
| 2009/0246738 A1 | 10/2009 | Karmaker |
| 2009/0311646 A1 | 12/2009 | Winsauer et al. |
| 2011/0300511 A1 | 12/2011 | Karmaker |
| 2013/0295517 A1 * | 11/2013 | Singer ............... A61F 5/05891 433/19 |
| 2015/0245888 A1 * | 9/2015 | Hasegawa ............... A61C 7/08 433/19 |

\* cited by examiner

SECTION A-A

ORTHODONTIC SYSTEM ANCHORING METHOD AND APPARATUS

RELATED APPLICATIONS

This patent applications is a continuation-in-part patent application of the patent application entitled "Orthodontic Appliance Anchoring Method and Apparatus", Ser. No. 13/487,822 filed Jun. 4, 2012.

BACKGROUND OF THE INVENTION

Field

This invention pertains to orthodontic anchoring and appliance attachment systems. Specifically, it refers to an orthodontic anchoring and attachment method for teeth connected to orthodontic appliances. These are custom made appliances designed on demand by the orthodontist for the anchorage needs and/or appliance development during one visit at the orthodontist. These appliances are affixed to temporary anchorage devices (TADs) and/or teeth and/or orthodontic appliances. Each custom appliance has in common mechanical fasteners with one or multiple orthodontic auxiliaries and, at least one flexible fit module (FFM), which is a flexible curable resin rope. The mechanical fasteners can be fitted to all traditional orthodontic appliances/auxiliaries. Between any of these fasteners the FFM is placed to complete the appliance. This invention simplifies orthodontic mechanics used by the orthodontist for tooth movement and alignment creating never seen before appliances, which incorporate current orthodontic auxiliaries, and blend them into a new innovative system. Fasteners are placed on teeth, TADs or appliances. Then segments of the FFM are adapted around the anatomy of the mouth to join fasteners together. Once the appliance is designed, adapted and fitted to the patient, it is cured to become a rigid leverage point or points to withstand oral and orthodontic forces required to move teeth. Tooth movement is simplified and made more efficient while time is minimized and patient comfort is improved.

State of the Art

Orthodontics and Dento-facial Orthopedics deal in the treatment of malocclusion (improper bites), mal-alignment of teeth and manipulating jaws during growth or with surgical intervention to improve oral facial esthetics, function, and oral health. Comprehensive orthodontic treatment utilizes many intra-oral and extra-oral appliances to achieve corrective measures. Most commonly orthodontic brackets are bonded to teeth and metal wires are inserted into the orthodontic brackets (dental braces), which are made from various metals or a more aesthetic ceramic material. The wires are generally affixed with elastic or metal ligatures and interact with the brackets to move teeth into the desired positions. Orthodontic appliances have historically been connected via custom bent wires connected from the teeth to the auxiliaries and/or appliances through laboratory procedures.

Stainless steel arch-wires can be bent, shaped, and tightened to achieve desired results. Newer Nickel-titanium arch-wires and other temperature-sensitive materials are routinely used for this purpose, but do not require bending. When cold, the arch-wire is limp and flexible, easily threaded between brackets of most configurations. Once heated to body temperature, the arch-wire will stiffen and seek to return to its original shape. These arch-wires create constant light forces on the teeth. Brackets with hooks can be placed, or hooks can be added to the archwire to affix elastics to pull teeth into alignment. The placement and configuration of the elastics is determined by the required course of treatment of each patient. Each month or two, the braces will be adjusted and modified as needed. The orthodontist will remove the colored rubber ties keeping the wire in place or the wire may be replaced or modified and rubber ties replaced as individual ties or a continuous chain is used to close space. Tooth positioning appliances are defined as all traditional appliances used in orthodontics including but not limited to brackets, bands, tubes, cleats, buttons, wires, caps, rapid palatal expanders, nance appliances, space maintainers, trans-palatal arches, distalization appliances, dental orthopedic appliances, custom bent appliances or any other appliance commonly used it the practice of orthodontics.

Temporary attachment devices or TADs are used as anchored points to secure elastics, springs or wire modules bent for a specific purpose. These elastic or metal modules use a TAD, which is fixed to bone and not connected to teeth for anchorage. Teeth are poorer anchor points because teeth move in accordance with Newton's third law—for every action there is an equal and opposite reaction. Thus when connected to large molars, smaller teeth are more likely to move further toward the molars. This creates a problem when a tooth is not to move. TADs have begun to solve this problem by adding anchorage to a tooth or groups of teeth allowing for biased orthodontic mechanics.

In additional to TADs and ancillary components orthodontics includes removable appliances, headgear, expansion appliances, fixed appliances and many other devices. These adjunctive appliances may be used to move teeth and jaw bones. Functional appliances, for example, are used in growing patients (age 7 to 14) to modify the jaw and their relationship. This therapy, termed Dento-facial Orthopedics, is followed by fixed multi-bracket therapy (see "full" //en-.wikipedia.org/wiki/Dental_braces ("braces") to align the teeth and refine the occlusion (see //en.wikipedia.org/wiki/Occlusion ("dentistry").

In many cases there is insufficient space in the dental arch for all the teeth to fit properly. There are two main procedures to rectify this problem. One is extraction: teeth are removed to create space. The second is expansion: the maxillary arch or upper jaw is made larger by using a palatal expander. The palatal expanders are secured to teeth to direct the expansion along the suture that separates both halves of the upper jaw. This is the suture that opens and subsequently fills in with new bone when a rapid palatal expander is used.

A number of devices are employed with round steel wires attached to fitted bands around teeth to direct forces and move teeth to correct a patient's bite. For example, Cope, U.S. Pat. No. 7,717,707 issued May 18, 2010 discloses an Orthodontic trans-palatal intrusion arch assembly secured with TADs to close open bites. It employs a number of trans-palatal arch wires connected to molar bands and TADs to direct forces along desired segments of the mouth. These wires are custom bent and formed to the patient and do not necessarily form a perfect fit. Consequently, additional welding and adjustment and/or lab work are required, resulting in multiple fitting visits. Cinader, Jr., U.S. Pat. No. 7,774,084 issued Aug. 10, 2010 creates a method by which implants can be placed more accurately using a template created with the aid of computers. The doctor can place TADs or other types of implants more accurately with this template technology device.

Conventional appliances must be welded and bent to fit the anatomy of the oral cavity. This requires: 1) fitting bands or brackets in the office and taking impressions of the teeth, 2) placing the fitted bands/brackets into the impression and 3) sending it to a lab for custom bending of steel wires, soldering of the wires to connect component of the appliance and/or making acrylic components of the appliance. After the laboratory production is completed the patient is brought back in to the orthodontic office where final bending adjustments are made to the appliance by the orthodontist. Typically these appliances contain brackets or bands fitted with hooks and bars welded in place from teeth to TADs or other appliances. These can be affixed to the arch-wire, bracket or TADs to secure to elastics, springs etc. to move teeth into alignment. This can result in ill-fitting jerry rigged devices, which can be uncomfortable for the patient and not ideal for the orthodontist.

The custom device and method described below avoids these problems by providing an easily fitted FFM connected to an anchoring system associated with TADs and/or appliances to the tooth/teeth. This FFM replaces the stainless steel wire and connects the different components of the appliance, and allows for immediate placement of an efficient, comfortable appliance with no lab work or impression requirements. This invention creates a new category of appliances to simplify orthodontic mechanics used to align teeth without welds, bending of wires, or multiple fitting visits. It thus alters current orthodontic practices, saves time, impressions and is beneficial to the patient and the Orthodontist.

OBJECTIVES

Some of the objectives of the present invention are to:

1) Create a new system to attach to and utilize temporary anchorage devices TADs for anchorage and revolutionize the attachment of traditional orthodontic appliances to teeth.

2) Simplify and generate efficiencies to orthodontic mechanics by allowing up righting and space closure of tipped molars by placing a bracket suspended in space and fixed to a TAD where the orthodontist would have the bracket if the tooth were ideally placed. This invention assists the orthodontist with many difficult orthodontic procedures including but not limited to: canted occlusion, impacted or un-erupted teeth, intrusion, extrusion, expansion, space closure or opening, and fixed stabilization of a tooth or teeth when movement is not wanted and additional anchorage is required.

3) Decrease treatment time and patient compliance requirements by improving the use of TADS which are screws inserted into the bone between the teeth for increased anchorage or to create points of fixed anchorage which can be manipulated to the advantage of the Orthodontist to move teeth.

4) Enhance utilization of traditional appliances by changing the way the appliance are fit and connected together using one or more flex fit modules (FFM), which are flexible curable resin ropes and clamps attached to traditional bands, brackets, appliances, TADs etc. These clamps and FFM are connected together providing a platform by which the orthodontist can adjust auxiliaries from TADS and/or appliances to the current brackets and systems to bias the orthodontic mechanics for the benefit of the patient and orthodontist.

5) Employ TADs used in conjunction with traditional brackets, wires, invisible removable aligners, and appliances to move teeth into the desired alignment by creating a new category of appliance or attachment apparatus.

6) Remove the requirement of impressions, lab work, utilization of preformed or custom bent wire used to connect appliance parts, and aftermarket soldering currently required to make and properly place orthodontic appliances. The FFM works in conjunction with or can entirely replace the wire or wires used to connect components of orthodontic appliances.

Specifically, this invention provides attachment devices from the TAD to a tooth or teeth either directly or indirectly. It also provides the ability to attach from a TAD to a free-floating point in space cantilevered to where the tooth is desired to arrive. This invention is used to create desired movement, or to stop undesired movement by being placed mesial or distal (in-front or behind) of a bracket and then being activated by traditional orthodontic mechanics to move teeth, thus avoiding undesired movement of anchored teeth. Between these new attachment devices a new flex fit module (FFM) is utilized to adapt to the anatomy of the oral cavity and provide a perfect fitting appliance in one visit with no lab work.

SUMMARY OF THE INVENTION

The invention comprises orthodontic TAD attachment devices, tooth attachment devices, and orthodontic appliance attachment devices, all connected to a tooth or teeth (via brackets/bands/orthodontic hardware/orthodontic appliances). The attachment is made using a clamp which connects to a Flex Fit Module (FFM) (curable flexible resin rope) at one end, which is then shaped to the patient's oral anatomy and fastened to another auxiliary clamp to attach to a tooth, appliance, TAD or be set to a point in space toward which the tooth will be moved. The FFM replaces the wire traditionally used to connect components of orthodontic appliances from tad to tooth to appliance in any combination. TAD, tooth, and appliance connections are custom designed and can be formulated in any order and number of attachments (connected to TAD, tooth, appliance) in any configuration to any part the oral cavity.

As used herein, the term "flex fit module (FFM) or resin rope" is a component of this orthodontic system allowing for the connectivity from tooth to orthodontic appliance or from one component of this system to another component of this orthodontic system which connects to any traditional orthodontic bracket, band, appliance or system. One example would be from a temporary anchorage device to an orthodontic auxiliary such as a tube, band, hook, button or bonded or non-bonded attachment which interfaces with a tooth to hold it in place or cause it to move. Another example is the connection between a band on a tooth and a nance, rapid palatal expander, space maintainer, holding arch or any other orthodontic device.

As used herein, the term "flexible structural component" is a structure used to alter the handling of the pre-cured resin rope (FFM) or the strength of the pre-cured or post cured resin rope. The flexible structural component is one component of an FFM and may not be required in all FFM resin ropes. The flexible structural component of an FFM may be a solid wire or a hollow tube of any diameter or shape to accomplish handling and strength requirements of a particular orthodontic use. It also may or may not be used to contain resins, components of resin their fillers or fibers. This structural component may be more flexible or less flexible dependent upon required usage and loads required for any given orthodontic purpose. The flexible resin component is therefore made from any material that fits the required force load and handling requirements. A partial list of these materials includes steel, stainless steel, surgical steel, nickel, aluminum, copper, tin, lead, iron, tungsten, magnesium titanium or any amalgamation of the above with additives to create proper strength and handling properties. These materials may also be treated by annealing, hardening or softening with heat or additives. Other materials that are used for flexible structural components include plastics, fibers, woven fibers, carbon fibers, metal fibers, cloth fibers, resin impregnated fibers or filaments which could be made into such a flexible structural component. These materials can be cut or made from additive manufacturing (3D printing) as required to produce said structure. These materials of metal of any variety or other materials can be porous, etched, scored, cut, perforated, laser cut with a symmetrical or asymmetrical grooves, lines, matrix patterns of any varied shape and may have any shape or cross sections along entire rope or at different portions of any given rope. The flexible curable component may encase internal elements or be imbedded a given rope. It can be of any cross-section and of different diameters. It may or not be flexible at parts and ridged at other parts or ends to accomplish attachment connections to other parts of this orthodontic system. The fasteners by which pieces are connected to teeth, directly to soft tissue, orthodontic appliances, other components or orthodontic auxiliaries may be accomplished as one piece with the flexible structural component at any ends or at any point or points along the resin rope (FFM). It can be solid at any point along said rope to accommodate fixtures, collars, clips, fasteners or for orthodontic uses or connectivity. It may or may not be cut, scored, perforated, symmetrically or asymmetrically to alter the direction the rope is likely to flex before and during placement or is likely to receive forces after placement and curing. The encasing or embedded structural component may be matrix or stent like lattice ma be in or around a curable resin forming a reinforced matrix rope when cured.

As used herein the term "fastener" is any connecting device which attaches any FFM to any other traditional orthodontic hardware, orthodontic appliances, orthodontic auxiliaries, flex fit wafers (FFW), to other FFM(s), or parts of this orthodontic system. Said fasteners which are also referred to as attachment devices connect one piece of orthodontic appliances/hardware/systems to another with a physical attachment such as a clamp, clip, hook, collar, wire lock, insert, chemically adhered junction, resin adhered junction, snap, weld, channel and groove, pin and lock, wire tie, insert clip or ball, cleat attachment, linkage, flexible junction, collar and sleeve, ball and joint, groove and snap, male and female inserts, friction junction with one way lock, friction junction with two way lock, or any mechanical unit which connects parts of this orthodontic system.

As used herein the term "component" refers to different parts of the orthodontic system. A partial list of components include various different flex fit modules (FFM's) or flexible curable ropes, fasteners, orthodontic appliances, temporary anchorage devices, hard tissue bone attachment plates, magnets, vibration devices, tissue penetrating orthodontic visible or non-visible lights, braces, extra-oral or intraoral orthodontic apparatus's, removable alignment devices, retainers, Bite correcting appliances, tooth holding appliances, teeth moving appliances, Orthodontic auxiliaries and Flex fit wafers which connect to other components of this system for orthodontic purposes.

As used herein the term "flex fit wafer" is a soft tissue interface which is connected to an FFM or orthodontic appliance which allows the direct contact with the soft tissues of the oral cavity such as a nance appliance which would be connected to one or more FFM(s) then connected to a bands or brackets on required teeth.

As used herein an orthodontic auxiliary is any linkage or connecting apparatus which can hold or activate orthodontic movement and the term of orthodontic appliance is one or more auxiliaries combined to create an appliance. The following is a group of orthodontic appliances and auxiliaries and not meant to be a complete list: a temporary anchorage device (TAD), bone plates, orthodontic hardware, removable orthodontic appliances, tooth holding appliances, fixed orthodontic appliances, space maintenance appliances, orthodontic braces, ligatures, clear removable aligners, a second FFM, a flex fit wafer, band(s), bracket(s), custom milled or additively manufactured brackets or bands, mesh pads, tubes, wires, orthodontic auxiliaries, hooks, buttons, elastics, elastomerics, inter-oral or extra-oral orthodontic appliances, active tooth positioning orthodontic appliance(s), magnets, visible and non visible light emitting appliances, vibration devices, appliances which deliver an electrical current(s) into the oral structures.

As used herein the term anchorage element is any appliance or auxiliary which has a fastener or fasteners attached or embedded or incorporated onto or fabricated within or welded to said appliance or auxiliary.

This invention is functionally efficient, and comfortably attached to one, two or multiple teeth and/or TAD and/or appliance by a clamp designed for that specific use. The invention also modifies current appliances by adding clamps to them. These clamps are then fitted with FFM's, which are shaped and connect to teeth, which are also fitted with clamps. The apparatus can attach to the orthodontic appliance via the arch-wire, which may pass through a tube (round or rectangular) that is part of the clamp. This tube is fitted to the mechanical fastener (clamp), which provides immovable stop to hold teeth in a particular position within the dental arch.

The connectivity from teeth to TADs or appliances using cut to length, flexible curable resin ropes (FFM) has not heretofore been employed. Adaptations of this appliance are fit and molded to the patient's oral anatomy and cured via heat, time, chemical or light curing, which fixes the apparatus between all its various custom attachments in place creating a newly place fixed custom appliance. The invention allows for a simple more precise use of forces on braces, arch-wires, and teeth or the appliances used to align teeth. Thus, this new anchoring appliance provides vectors with fewer unwanted side affects to align teeth using braces, arch-wires, and orthodontic appliances. The orthodontist can design biasing pressure as needed to obtain selective movement of teeth.

Specifically, the invention comprises at least one FFM curable flexible resin rope of varied diameters and length secured by TADs, teeth (via bands or brackets) and/or appliances, each having mechanical fasteners structured to secure segments of the flexible resin rope to its end use attachment. The FFM resin rope in a first mode is flexible and of a length to be positioned and adapted within the mouth along desired segments of the teeth, gums, palate and buccal and lingual portions of the oral cavity in both the mandible and maxilla. The resin rope is then attached to another clamp to anchor, attach, or connect to a desired structure, (i.e. TAD, tooth or appliance) in the oral cavity with the purpose alignment of the human dentition. In a second mode after being placed in the desired position, the resin rope is cured and hardened with light, heat, or chemicals to rigidly hold its position during the application of the biasing pressure to the teeth (orthodontic force). This provides exact placement of desired anchorage points to teeth, TADs, appliances or points in space for the orthodontist to create desired vectors on teeth. Pulling, pushing, erupting, intruding, rotating, torque, tipping and bodily movement of teeth using braces, arch-wires, TADs and tooth straightening appliances move the teeth more efficiently using forces biased based on the needs of the individual patient.

Orthodontic appliances are currently fabricated of stainless steel components, i.e. screws, pistons with springs, or wire custom bent or pre-formed to serve a function. They are then welded to bands or brackets. This invention can be connected to all of these devices without wires or bending to connect them. This is a one-visit appliance fit utilizing the Flex Fit Module (FFM) and clamps at both ends of orthodontic device now connected without custom bent wires.

In one embodiment, the mechanical fasteners are hinged with curved locking jaws structured to secure to segments of flexible resin ropes. This can be repeated with unlimited numbers of locking jaws (clamps) used along any portion of the resin rope. Any attachment can be designed in conjunction with these clamps to serve any anchorage issue in orthodontics. The diameter of the closed clamp is smaller than the resin rope to create a mechanical lock. This mechanical lock can be achieved with teeth or protruding wedges which bites/penetrates into the FFM tube and/or resin creating a lock from the clamp to the FFM. There are cut outs or windows in the clamp to ensure the flexible rope is cured properly. The windows also serve as mechanical locks because some of the FFM flexible tube or resin protrudes into the cut outs or windows and extends past the clamp and around its borders to mechanically lock it in place as it is closed. Using these principles the ropes/FFM and jaws/clips can have any required diameters to meet the force required by a specific anchorage issue or a particular appliance to be fitted with this system.

In another embodiment, the TAD is inserted into the bone with its head protruding out of the tissue. A cap that fits over the head of the TAD is fitted with a clamp (one piece), which accepts the FFM and is placed on the TAD. A bracket or band also fitted with a clamp is bonded to a tooth. The FFM is cut to length and shaped around the anatomy of the mouth from clamp to clamp. The jaws of the clamps are closed and the FFM between the clamp on the tooth and the clamp fixed to the TAD are cured. After curing the device becomes a solid system anchoring the tooth with the TAD. This system can be repeated using any appliance used in orthodontics, which is fitted with a clamp to any tooth fitted with a band or bracket fitted with at clamp. It is also possible to attach between these two ends another fastener/clamp fitted with any auxiliary such as hook or bracket to the FFM for orthodontic use.

Mechanical locking devices or clamps or clips can be configured as closing jaws or snap fit covers where two separate pieces snap together to form the clamp with teeth to bite into the resin rope and fix the FFM mechanically in place. (as seen in cross section of expansion screw shown in FIG. 4b)

At least one curable flexible resin rope has segments secured by the mechanical locking devices in a first mode where the rope is flexible for positioning within the mouth and contoured around the anatomy of the oral cavity of the patient. Various auxiliaries can be positioned around the mouth and in conjunction with traditional orthodontic appliances to created beneficial placement to aide in the alignment of teeth and to modify growth of the jaws, when appropriate. Once in position the custom appliance including the curable resin rope (FFM) and its fasteners are cured into one piece and hardened with light, heat, or chemicals to rigidly hold its position. Biasing pressure is then employed to prevent some teeth from moving while encouraging movement of other teeth using a TAD or Multiple TADs for anchorage.

One embodiment of a mechanical locking device has hinged jaws with teeth that interlock when closed to secure around a desired segment of the flexible resin rope. The hinged jaws include at least one opening through which a portion of the resin rope protrudes into when the jaws are closed to prevent the rope from slipping, when hardened. The diameter of the FFM is larger than the jaws when closed. In another variation the locking jaws can be of the same diameter of the FFM, if the inner parts of the jaws are structured to provide retention through a mesh pad system to lock the resin in place when cured.

The mechanical locking device may include an orthodontic tube or central channel structured to allow an arch-wire to slide through. It may also be fitted with a bracket, cleat, or hook to which springs or elastics may be affixed to apply vector pressure. In another variation, the central channel of a slide is rectangular in shape to secure to the arch-wire to prevent its twisting; thus providing rotational force to the tooth positioning appliance and affixed tooth when the arch-wire twists. The auxiliary device is manipulated via wire bending to place the auxiliary at a point in space, which is beneficial to orthodontic movement with the removable wire temporarily fitted into a tube or bracket before the FFM is cured. The FFM is fitted to the fastener and is held in place temporarily by said wire. When the FFM is attached to the fastener is cured, the wire is removed for the auxiliary to accept activation.

An orthodontic space maintainer or a TAD(s) may be connected to an arch-wire where an FFM is adapted around tissues and orthodontic hardware to allow the tube or bracket to be placed on an orthodontic arch-wire via a central channel (tube), which allows the orthodontic bracket or tube to slide and be placed at any position along said arch-wire. After curing of the FFM, the tube or bracket becomes locked in place and a hook or cleat secured to the sliding attachment can be connected to or by other auxiliaries such as springs and elastomerics for application of orthodontic biasing forces delivered to another tooth or teeth.

One embodiment of the tooth positioning appliances comprises teeth (banded) with hinged jaws to interlock when closed to secure around a desired segment of the flexible resin rope (FFM). The mechanical jaws when shut are of a smaller diameter than the FFM and because windows are cut into the jaws of the mechanical fasteners to allow the uncured FFM to be expressed or protrude through window when jaws are closed. Once cured the mechanical junction is complete.

A cleat, hook or bracket may be affixed to the hinged jaws to provide another anchoring point for the orthodontist to attach springs, wires or elastic components as needed to complete a custom appliance.

In another embodiment, the mechanical locking device comprises hinged jaws with teeth, grooves, dimples, channels affixed and interlocking together (both male and female portions of clamp) when closed to snap and clip together to hold clamp shut and secure around a desired segment of the flexible resin rope FFM. The teeth or grooves inside the clamp are different and used to bite into the FFM itself to lock the FFM in place.

In another embodiment, the orthodontic anchoring apparatus includes at least four Flex fit modules FFMs affixed with a clipping clamp to an expansion screw in the palate of the mouth. The opposing teeth on each side of the maxillary arch (two teeth on each side of the arch) of the mouth are fitted with brackets with mechanical locking devices (clamps). After the four FFMs are locked into place via the clamps, formed and cured the arch is ready for expansion.

To secure rapid palatal expanders, curable FFM flexible resin rope segments with first ends secured by the mechanical locking devices or jaws attached to the teeth at one end and to the expander at the second ends. The FFM's in the first mode are flexible and positioned around the anatomy of the mouth to attach both ends of the FFM. Once in position the FFM's are cured and hardened with light, heat, or chemicals to rigidly hold its position to make the appliance solid during tooth/jaw movement. The FFM rope segments, now cured, rigidly fix in position the rapid palatal expander so that its separation structure (screw), when activated, applies lateral separation pressure to the teeth to widen the palatal suture of the roof of the mouth. This invention allows expanders to be placed to either a TAD, a tooth, or both using clamps fit to the expander.

The flexible resin ropes/flex fit modules (FFM) are made of light, heat, or chemically curable resins which can be mixed with fillers or fibers to form a composite material. The curable resin can include but is not limited to epoxies, acrylates, cyanoacrylates, silicones, polyurethanes, or polyureas. It is preferred that the curable resin be activated by light and be based on acrylate resins with a photoinitiator that is activated by either UV or visible light. The acrylate material could be a combination of di-functional and tri-functional resins and are most commonly composed of bisphenol A-glycidyl methacrylate (Bis-GMA) monomers or Bis-GMA analogs. Other functional acrylates can be added as reactive diluents to achieve certain physical properties such as flow-ability for ease of handling. As with other composite materials used for dental composite fillings, the preferred resins typically consist of an oligomer acrylates, such as a (Bis-GMA) or urethane dimethacrylate (UDMA), a reactive diluent, and a filler. Oligomer Bis-GMA analogs can vary with the addition of polyethylene glycol (PEG) monomers incorporated into the molecule. Urethane methacrylate oligomers can also be used with both di- and tri-functionality with or without PEG constituents. Reactive diluents include triethleneglycol methacrylate (TEG), low molecular weight trimethacrylates or other PEG based methacrylates. The compositions vary widely, with proprietary mixes of resins forming the matrix, as well as engineered filler materials depending upon the composite properties required. The FFM can be made with or without a flexible rubber/plastic tube of varied thickness which encases the resin material and allows for better working properties. This can also be described as a resin filled tube which is flexible. The tube wrapping the resin can be configured with varied widths and different materials and varied chemical/molecular makeup to adjust its properties.

Filler materials can be based on organic or inorganic materials. Examples of organic fillers can be nanometer or micrometer size particles of polymers based on polystyrene, nylon, or others. Examples of inorganic fillers can be nanometer or micrometer size particles based on silica, alumina, or other inorganic metal oxides or ceramics. Filler materials are used to adjust key properties of the resins such as mechanical properties and viscosity. Nanomaterials can also be used as fillers, such as carbon nanotubes or nanowires based on metals or metal oxides. A coupling agent such as silane may be used to enhance the bond between the components. Fiber materials can also be added to enhance the mechanical properties of the resin composite. Fiber materials can be made from carbon, glass (silica or other inorganic oxide), polyester, polypropylene, or other polymers and act as reinforcing rods to improve the overall stiffness and strength of the composite before and after curing.

In the preferred embodiment of the FFM, a photo initiator is used to cure the composite material that decomposes into free radicals when exposed to light to initiate the polymerization reaction. Photo initiators that decompose under visible light (wavelengths between 400-700 nm) are typically used in dental composites. Examples of photoinitiators include but are not limited to camphorquinone (CQ), phenylpropanedione (PPD) or trimethylbenzoyl-diphenylphosphine oxide (TPO). A catalyst or co-initiator may be included to control its speed. Co-initiators are typically tertiary amines such as ethyl 4-dimethylaminobenzoate.

The orthodontic anchoring device thus provides an improved easily fitted resin rope FFM which can be adapted anywhere a metal wire was historically bent and shaped for appliances such as but not limited to space-maintainers, rapid palatal expanders, trans-palatal arches, labial bows on retainers, anchoring systems associated with TADs and tooth positioning appliances. Forces can be directed through the FFM and vector can be individualized for better alignment of teeth. No lab work, custom bent wires, or multiple fitting visits are required.

The hinging jaws or clamps are just one iteration of other clamps, which will utilize the same overlying technologies and principles but may be different in their design, size, materials or mechanical workings. The hinging jaws or clamps may connect to a fastener or any connecting device or mechanism which allows for a physical, mechanical or chemical connection between any orthodontic device, equipment or one or more FFM(s) for orthodontic purposes. Likewise the Flex fit module or FFM including its resin makeup and it's tube or wrap requirements may be designed to fulfill the same function but can be designed with different shapes, thicknesses and materials but used for the same uses described here within.

For example, the invention may be adapted for use with invisalign type appliances. This requires a tooth anchoring structure designed to fit flat onto the lingual or buccal surface of a tooth/teeth via a bracket/band, which follows the profile of the of the anatomy of the tooth tightly as to enable the placement of a plastic invisible removable aligner or retainer over the combined tooth and band/bracket structure. The attachment maintains a thin, low profile tooth attachment bracket/band and continues apically, exiting the invisalign appliance and extends around the anatomy of the soft and hard tissues of the palate buccal/lingual mucosa on either/both the maxilla or mandible. It extends past the border of the overlaid plastic invisible removable aligner so as to be unencumbered by said aligner. At which point, a mechanical clamp accepts the first end of the FFM. Then the second end of the FFM is attached to at least one TAD with a mechanical fastener fitted with an attachment for the TAD (TAD cap). This attachment attached to the tooth has a removable cap placed over the clamps for smooth impression release and/or scanning of the teeth when the attachment is placed on teeth before an impression/scan is taken for fabrication of the appliance. This invisalign orthodontic appliance variation provides anchorage for the tooth/teeth during treatment with invisible removable clear plastic appliances and will allow for biasing forces with the use of invisible removable appliances.

In another embodiment, the tooth anchoring structure is designed to fit flat onto the lingual or buccal surface of a tooth/teeth via a bracket/band, which follows the profile of the anatomy of the tooth so as to not inhibit the placement of a plastic invisible removable aligner or retainer over the combined tooth and band/bracket structure.

This variation may be adapted with an FFM with first and second ends. An attachment with a removable cap, which maintains a thin, low profile and continues apically around the anatomy of the soft and hard tissues of the palate buccal/lingual mucosa on either/both the maxilla or mandible is included to extend past a border of the overlaid plastic invisible removable aligner leaving an unencumbered segment. The aligner is cut to allow placement in a low, thin profile with small lingual/buccal or in and out profiles, which extend below the level of the gingival margins. Beyond the boundaries of the aligner are placed FFM(s) to hold a tooth or teeth in place and assist in orthodontic anchorage of attached teeth. Where the bracket attachment and the FFM continue, allows placement of the plastic invisible removable aligner/retainer. A mechanical clamp is affixed to the unencumbered segment to accept the first end of the FFM attached to at least one TAD. The second end of the FFM has a mechanical fastener fitted with an attachment for the TAD structured so that the removable cap covers the clamps and the attachment provides a smooth impression for scanning before impressions or scans are taken.

These orthodontic anchoring apparatus with tooth anchoring structures, clamps, fasteners and appliances are made of metal or metal amalgamations/alloys components via mold injection or milling or casting techniques, which may or may not include stainless steel, molybdenum copper, tin, nickel, silver, gold, titanium, aluminum, and other similar materials.

The FFM curable flexible rope may be a resin filled tube. The resin within the tube can be chemically adjusted to achieve different physical characteristics including slump, firmness, wetness, malleability, flexibility, strength, hardness, flowability, curability properties and other relevant properties. The tube surrounding or encasing this resin also can be similarly modified by altering materials or width of tube to change its physical properties for the mechanical clamping or biting into via clamp requirements, and also those other properties mentioned above for the resin.

In still another embodiment, the FFM includes a flexible moldable skeleton allowing for manipulation, molding, contouring, and adding strength to the FFM to temporarily hold in a molded position in a first mode until cured in a second mode. The FFM flexible moldable skeleton may comprise and endoskeleton embedded in the matrix, or a bendable semi-rigid mesh or lattice like exoskeleton encasing the curable resin material. The semi-rigid mesh or lattice like exoskeleton defines spaces which allow light to penetrate for curing the curable resin material.

The flexible structural component can be made to have no perforations and thus can be solid segment or a non-perforated section of the rope with the same shape or flat or any shape to accommodate a physical, mechanical, or chemical fastener of any type at any given point along an FFM or at any of its end(s) to accommodate fasteners such as collars, clips, clamps, friction attachments, ball and socket, channel and groove, ligature, nut and bolt, screw to surface, male into female sliding receiver with or without grooves, or any other mechanical, physical or chemical fastener(s) used for orthodontic appliances and their connectivity to an FFM.

The FFM is manipulated to fit around the oral structures and is attached to a fastener attached to a tooth fitted with a bracket, custom milled bracket, or band bonded to said tooth to secure second ends of the FFM to the tooth. After curing the FFM the tooth is connected to a TAD fixed into the bone.

This tooth can now be an anchor to move other teeth using traditional orthodontic hardware which is attached on another side of a tooth. This same arrangement can be accomplished by FFM being attached at its second end to a fastener which is not connected to a bracket or band, but is connected to a rectangular or round molar tube or bracket fitted with a fastener to connect the tube or bracket to an arch-wire. It is slid adjacent to and in contact with a traditional bracket affixed to a tooth using traditional methods, but once the FFM and bracket are placed in contact and cured, the traditionally placed bracket or tube is held from moving along the arch-wire. Movement is stopped because the FFM attached tube prevents its sliding on the arch-wire in one direction and thus the tooth is held fixed to accomplish the same goals as were previously described.

The clamps mechanically or chemically bond or attach to the FFM when closed. Mechanical clamps physically attach to the FFM via teeth/protuberances/mesh, which clamp into and bite the tube and/or resin components of the FFM. Chemical clamps may bond to the FFM using teeth/protuberances/mesh attached to the clamp to create a physical pressure bonding attachment. The FFM may also interlock through a hole, window or end of clamp, when it is closed, as it will be expressed forcefully when clamp is closed and the FFM will be express through window/hole or end of clamp.

The orthodontic system modifies current orthodontic appliances to allow for custom insertion then adaption around hard and soft tissues of the oral cavity by changing in part or entirely the wires which have been traditionally used in orthodontics with various sized and shaped, including some or all of various components of the this systems flex fit modules or FFM(s). Also this system replaces the traditionally acrylic plastic portions of appliances or the tissue contacting portions of appliances with flex fit wafers which are flexible and light curable and accept FFM(s) to integrate into this orthodontic system. These modified appliances are used for any or all orthodontic purposes within the oral cavity and can be attached to oral structures or to lay upon oral structures and can replace any commonly used orthodontic traditional appliance such as an rapid palatal expander, unilateral/bilateral space maintainer, Nance holding appliance, functional appliances, intra-arch or inter-arch orthodontic appliances, fixed or removable orthodontic appliances, removable clear aligners, retainers, bite openers, occlusal coverage appliances, intraoral or extra oral appliances, molar distalization appliances, expansion appliances, bite modifying appliances. Or they can be used in conjunction with traditional bracket system such as clear or metal brackets, removable clear appliances, custom fabricated and designed orthodontic systems or simply used to introduce an orthodontic auxiliary or auxiliaries to existing traditional systems such as a cleat, hook, button clamps, fasteners, spring, piston, elastomerics, open or closed coil, bracket, tube, sliding or stopped arch-wire connection device, screw, lock, bolt and nut, stop, ligature, retraction device, power chain, TAD, head gear, traction device, visible light emitting device, vibration apparatus, or any other auxiliary, which is connected to this system using one or more of its components for orthodontic or orthodontic orthopedic purposes.

BRIEF DESCRIPTION OF THE DRAWINGS

The patent application file contains at least one drawing executed in color. Copies of this patent or patent application publication with color drawing(s) will be provided by the Patent Office upon request and payment of the necessary fee.

DESCRIPTION OF THE ILLUSTRATED EMBODIMENTS

Figure 1:
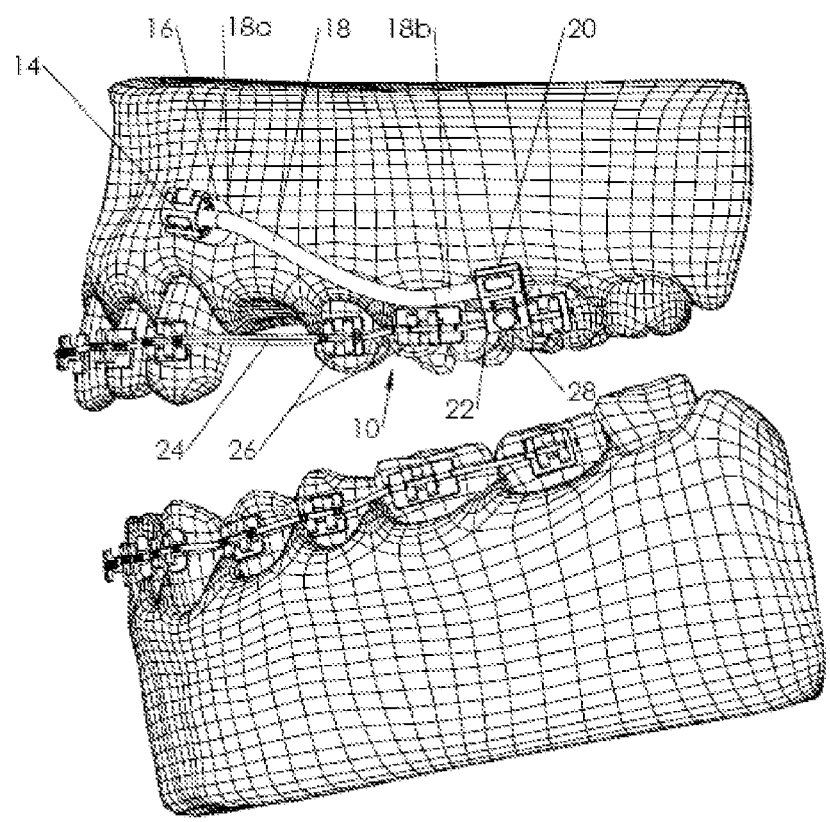
FIG. 1 is a perspective view of one embodiment of the invention with a double TAD mounted along the gum line above the teeth.

Examples of the present invention are illustrated in the following figures. FIG. 1 is a perspective view of one embodiment of the invention 10 mounted along the gum line above the teeth. A temporary anchoring device (TAD) 12 better shown in FIG. 7 with a mechanical locking device or clamp 14 attached to its head 16 is positioned between the teeth to the bone to provide a fixed anchoring point. One end 18a of a flexible curable resin rope 18 is secured by the mechanical locking device or clamp 14 of the TAD 12. The other end 18b is secured to a mechanical locking device 20 affixed to a tube clip 22, which accepts an archwire 24, and slides along the arch-wire 24 secured by braces 26. This appliance 10 is attached to a TAD above the teeth and to an orthodontic tube 22 with the arch-wire 24 passing through the tube 22. This use may require two separate TADs 12 to prevent rotation of an appliance as shown in FIG. 1.

Figure 5:
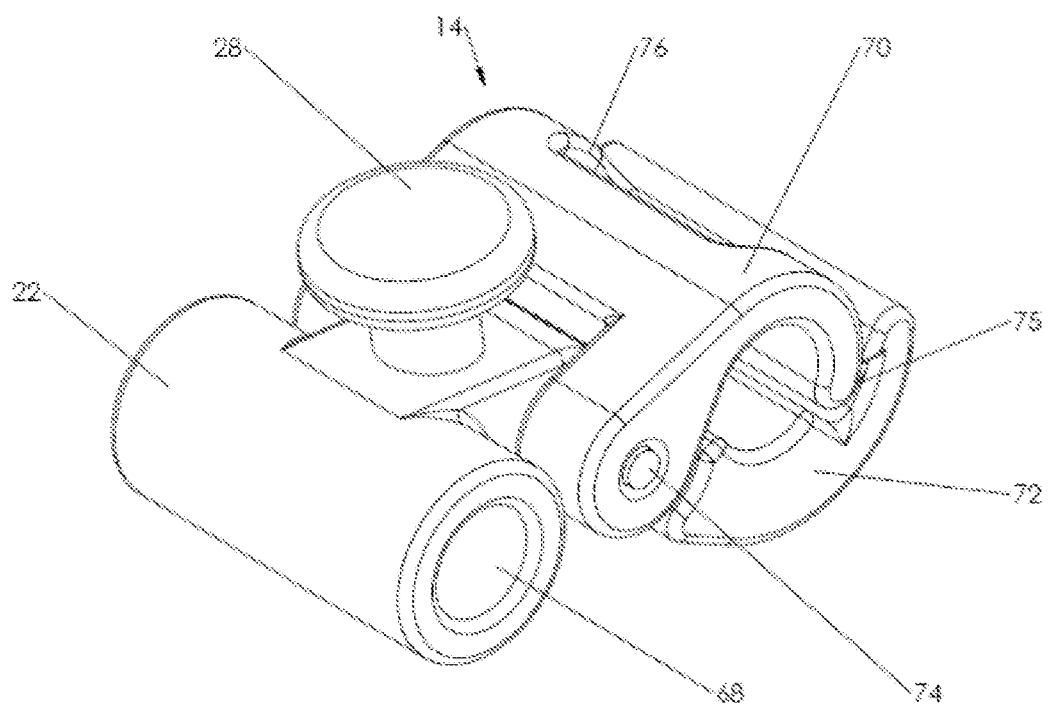
FIG. 5 is a perspective view of a mechanical locking device clamp or jaws.
Figure 6:
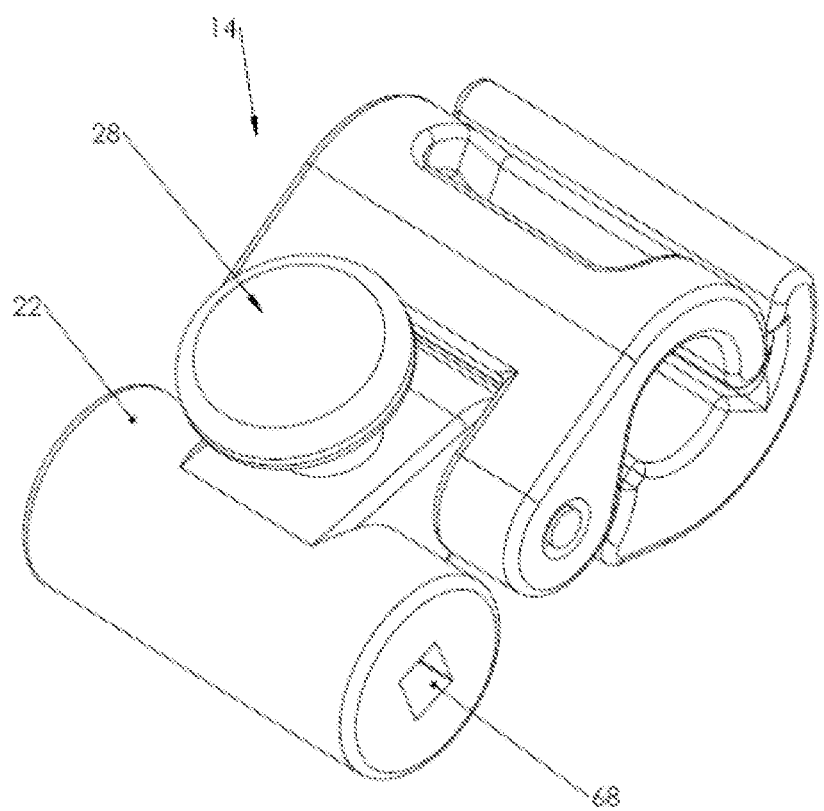
FIG. 6 is a perspective view of another mechanical locking device.

A cleat 28 shown in more detail in FIGS. 5 and 6 is attached to the mechanical locking device or clamp 20 to provide an anchoring point for elastic (not shown). Thus positioned, the resin rope 18 is cured with light, heat, chemicals or time to securely hold rigid the cleat 28 in fixed position to allow the teeth to move in a desired direction.

Figure 2:
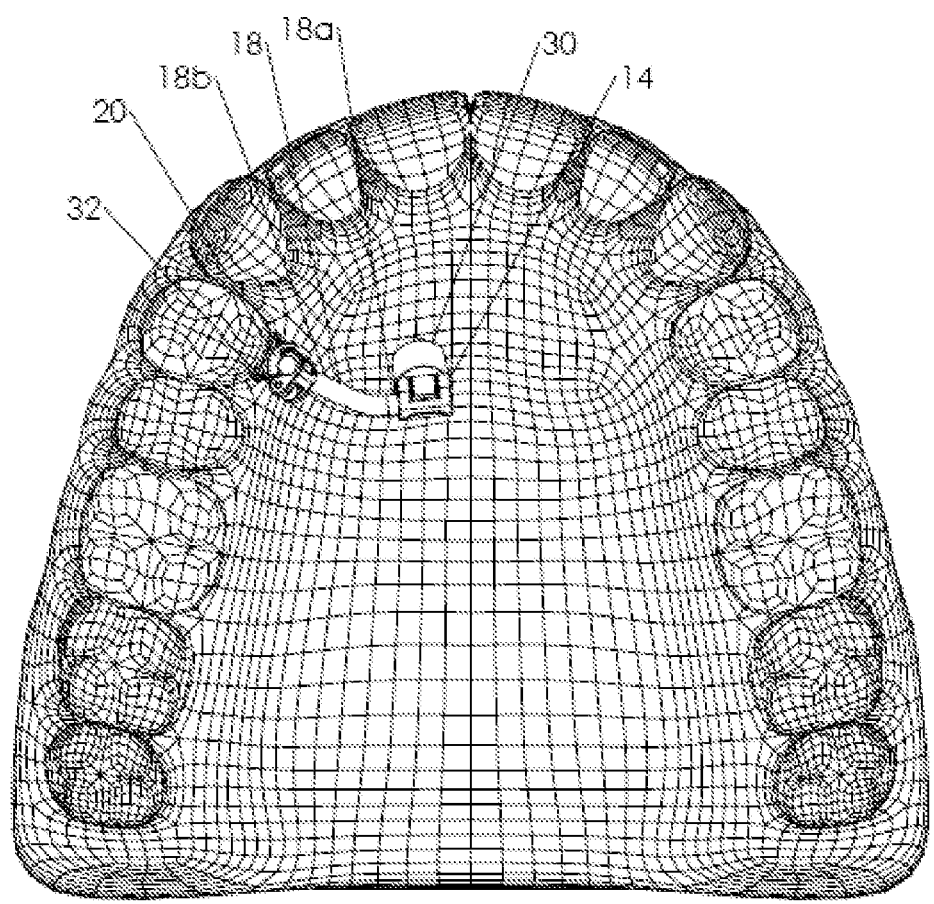
FIG. 2 is a perspective view of another embodiment of the invention mounted along the palate of the mouth.

FIG. 2 is a perspective view of another embodiment of the invention 10 mounted along the pallet to secure a desired tooth in position. This tooth can now be acted upon with traditional orthodontic methods and not moved. A TAD 12 with a mechanical locking device or clamp 14 attached to its head 16 (not shown) and a lingual bracket 30 is secured to the roof of the mouth. One end 18a of a curable resin rope 18 is then secured by the mechanical locking device or clamp 14 of the TAD 12. The other end 18b is secured by the mechanical locking device 20 of a band 32 fitted to a tooth in position. The resin rope 18 is then cured with light, heat, chemical or time to rigidly secure the banded tooth in fixed position relative to the TAD 12

The curable flexible resin rope, flex fit module or FFM, all hereinafter referred to as (FFM) 18, is moldable to the anatomy of the oral cavity and has variable diameters selected to withstand biasing forces when cured. It is then adapted around the anatomy of the palate and fit to a locking device clamp 20, which is attached to the TAD 12. After curing this is complete anchorage for the bicuspid.

Figure 3:
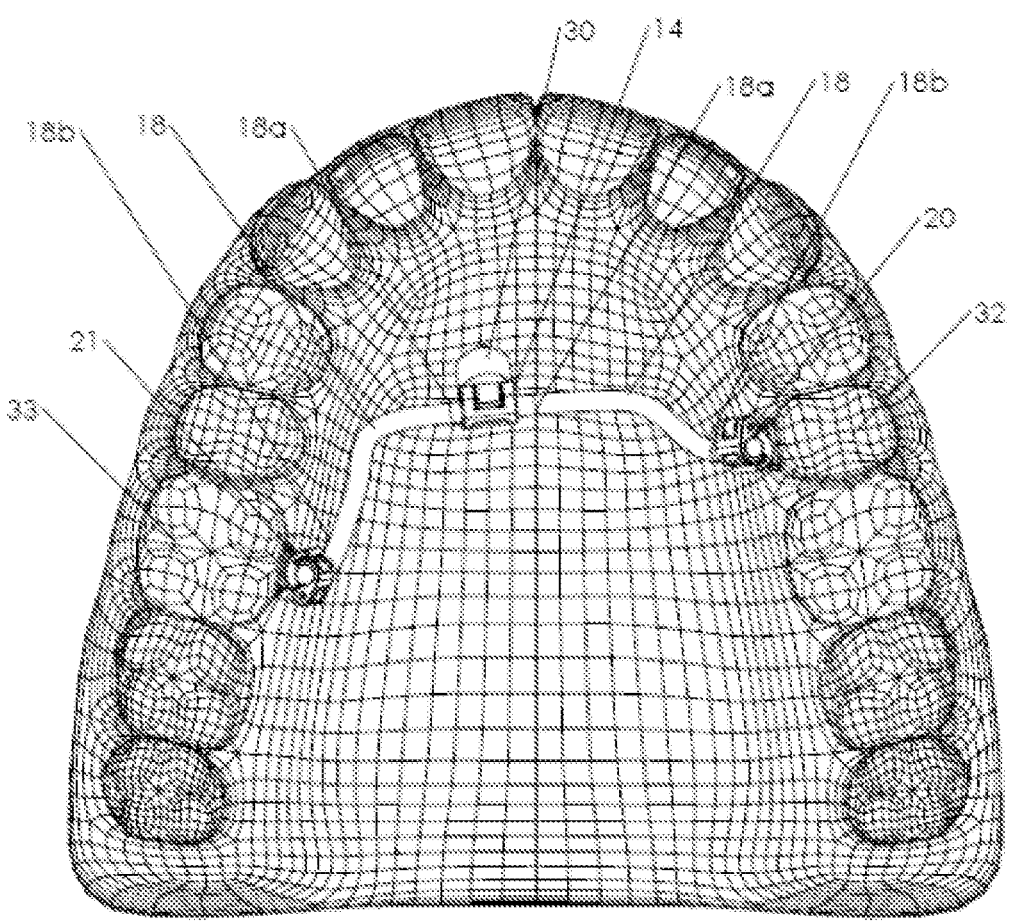
FIG. 3 is a perspective view of another embodiment of the invention mounted along the palate of the mouth.

The FFM 18 is a new category of orthodontic appliances whose primary functions include:
   i. Adaptation to the patients anatomy
   ii. Replacement of current custom bent wires to connect from tad to tooth, appliance to tooth, tooth to tooth, tad to bracket, tad to band, appliance to band or bracket, band/bracket to auxiliary, tad to auxiliary, band/bracket to acrylic pad, tad to acrylic pad, appliance to acrylic pad.
   iii. Elimination of lab work fabrication with one visit placement of custom made appliances FIG. 3 is a perspective view of another embodiment of the invention 10 mounted along the upper arch of the maxilla. This appliance 10 is fitted to a molar and a bicuspid via brackets 32, 33 fitted with clamps 20, 21. An FFM 18 is then adapted from one to the other and another mechanical locking device clamp 14 fitted with a lingual bracket 30 is attached to a TAD 12 secured to the roof of the mouth, holds ends 18a, 18b of the FFM 18 in position. It is then cured to achieve complete anchorage. The resin rope 18 is required to fit together between the attachment ends of all these appliances. Within these scanned images, the flex fitting resin is easily adapted to the anatomy of the oral cavity. In summary, the ends 18a, 18b, are secured by mechanical locking devices 20, 21 of tooth bands 32, 33. Once in position, the resin rope 18 is then cured with light to rigidly hold the two banded teeth in fixed position relative to the TAD 12.

Figure 4:
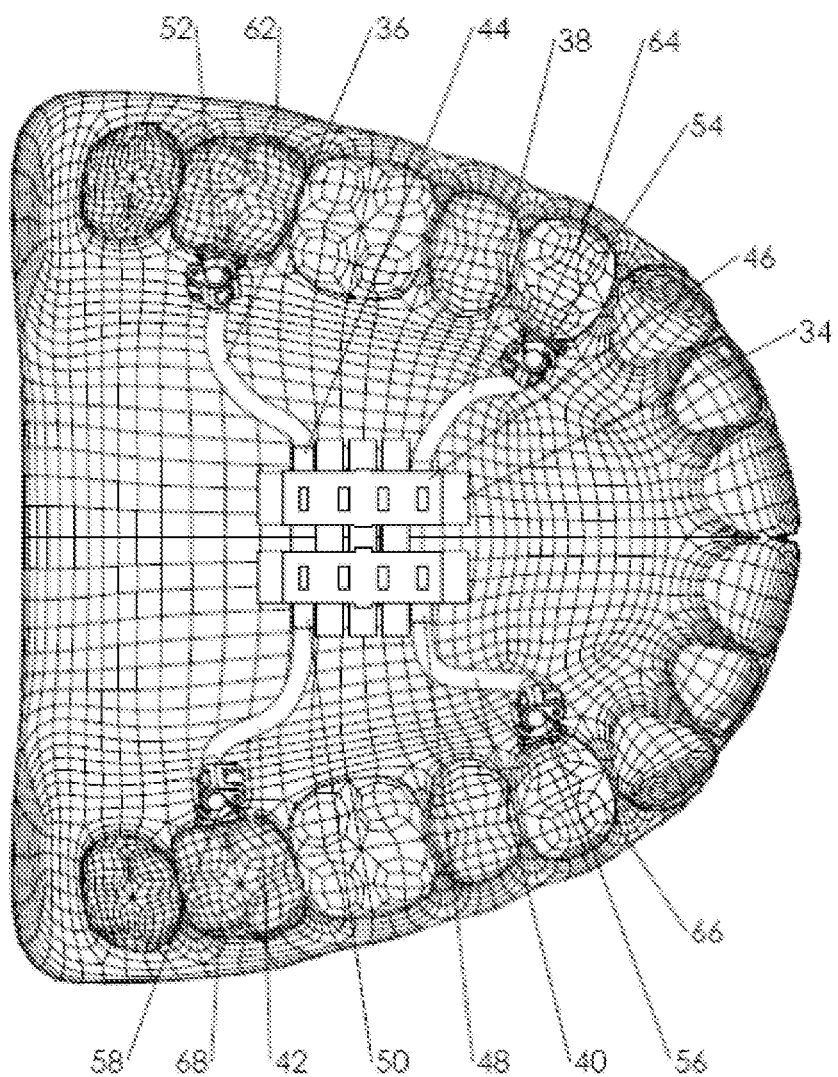
FIG. 4 is another embodiment of the invention mounted to a palatal expander mounted to the upper arch of the maxilla.

FIG. 4 is a perspective of another embodiment of the invention 10 mounted to a rapid palatal expander (RPE) 34 mounted to the upper pallet of the mouth. The RPE 34 is attached to the teeth via bands 62, 64, 66, 68 fitted with clamps 52, 54, 56, 58. FFMs 36, 38, 40, 42 are used to attach the teeth to the screw activated RPE 34. Once ends 52, 54, 56, 58 are secured to clamps 52, 54, 56, 58, and ends 44, 46, 48, 50 are secured by the RPE 34, the FFMs 36, 38, 40, 42 are fit to the anatomy and clamped into place. The RPE appliance is the cured to rigidly hold the palatal expander 34 in position and ready for activation. When activated, the RPE 34 applies spreading pressure to the four teeth expanding the suture of the palate to widen the bite.

Figure 4A:
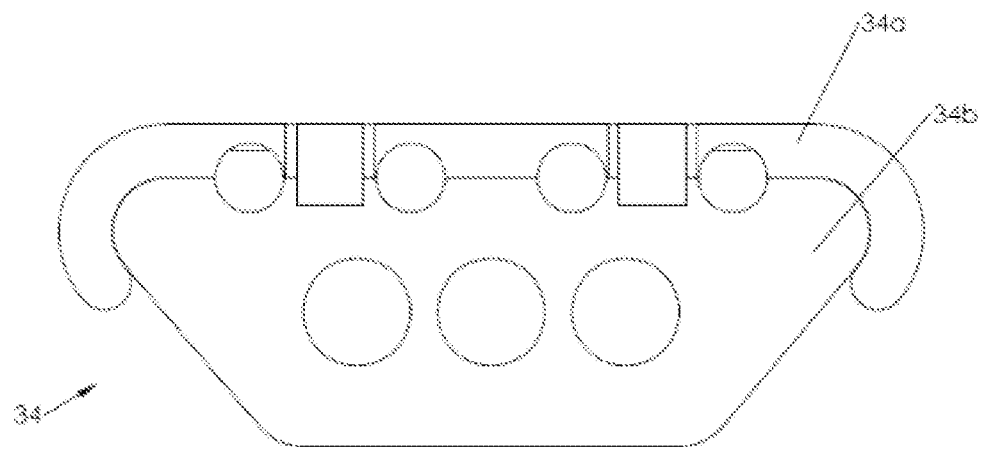
FIG. 4a is a cross section of the embodiment of the (RPE) palatal expander screw with FFM notches built into appliance of FIG. 4.
Figure 4B:
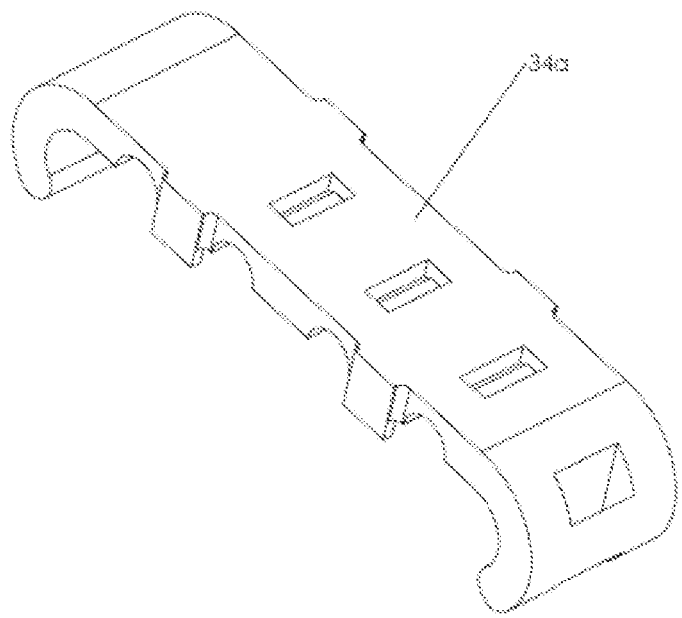
FIG. 4b is a perspective view of an RPE palatal expander screw cap that secures top portion of FFM when snapped in place over screw to secure FFM segments.

FIG. 4*a* is a cross section of the embodiment of the palatal expander RPE 34 of FIG. 4 showing its components 34*a*, 34*b*. The RPE cap 34*a* is secured to the RPE base 34*b* to hold the ends of resin ropes FFM 36, 38, 40, 42. FIG. 4*b* is a perspective view of the RPE cap 34*a* shown in FIG. 4*a*.

FIG. 5 shows appliance 14 is fitted with a round tube clip 22 with a tubular bore 68, which can accept arch-wires 24 or standard auxiliaries used in orthodontics.

This tube clip 22 has a round tube 68 with tubular bore 68 to slide along an archwire 24. The tube clip may have a rectangular bore 68 as shown in FIG. 6. The locking device 14 has curved hinged jaws 70, 72 held by a pin 74, which are structured to secure there between desired segments of FFMs 18 when locked by the hinged jaws 70, 72. One of the hinged jaws 70 contains an opening 76, which allows the FFM 18 to expand therein when the jaws 70, 72 are closed. When cured, the protruding segment of the resin rope 18 prevents the jaws 70, 72 from sliding along it.

FIG. 6 is a perspective view of another mechanical locking device 14 with a cleat 28 and slide 22 similar to that shown in FIG. 5. This clamp 14 is fitted with a cleat 28 to attach elastomeric ties. It also is fitted with a tube 68 with a square bore 68 to accept rectangular arch-wires allowing for torque to be introduced when needed. This slide 22 square hole 68 rigidly holds to the arch-wire 24 so that when it twists rotational pressure is applied to the mechanical locking device 14.

Figure 7:
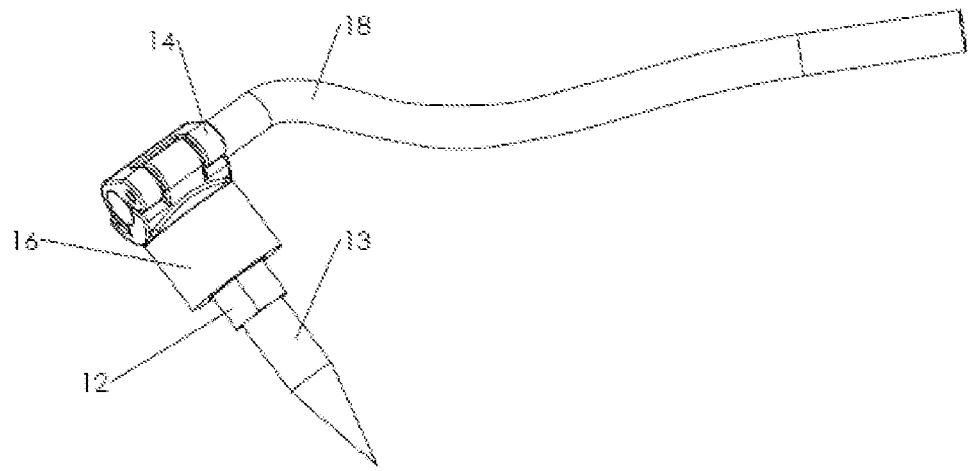
FIG. 7 is a perspective view of a mechanical locking device affixed to a temporary anchoring device.

FIG. 7 is a perspective view of a mechanical locking device 14 affixed to the head 16 of a TAD 12. The TAD 12 has an anchoring shaft 13, which is temporarily driven or screwed into the bone to secure the TAD 12 in position.

Figure 8:
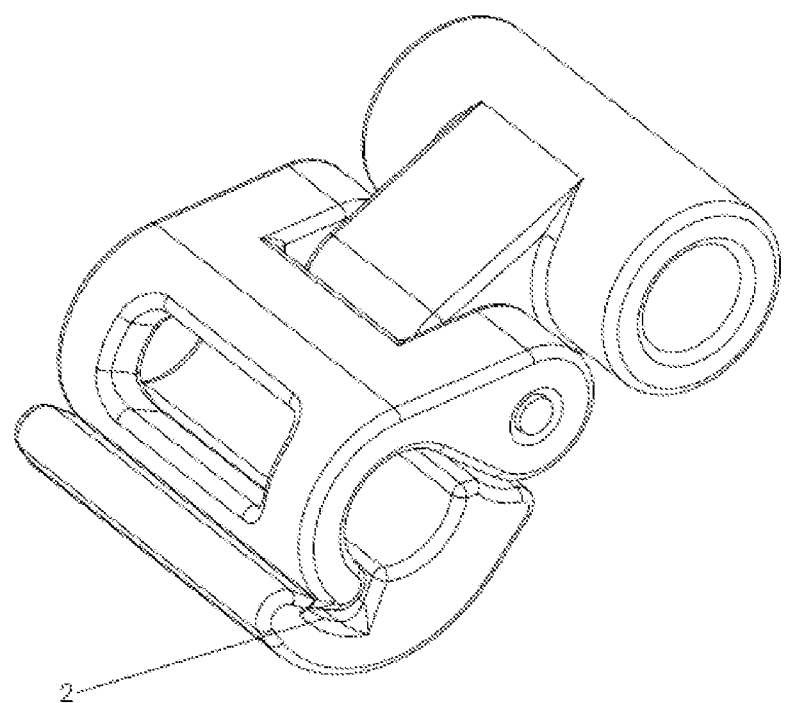
FIG. 8 is a top perspective view of another embodiment of a mechanical locking device.

FIG. 8 is a top perspective view of another embodiment of a mechanical locking device clamp 14 without a cleat 28. This perspective view better shows the openable locking structure of the jaws 70, 72.

Figure 9:
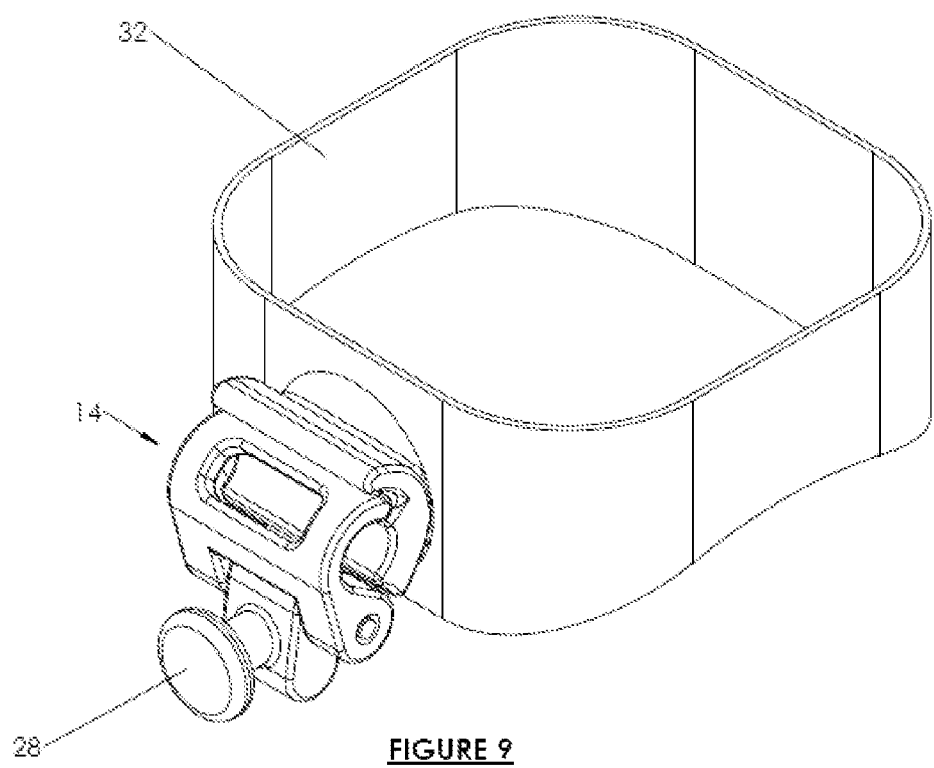
FIG. 9 is a perspective view of an embodiment of a mechanical locking device affixed to a band fitted to a tooth.

FIG. 9 is a perspective view of an embodiment of a mechanical locking device clamp 14 affixed to a tooth band 32.

Figure 10:
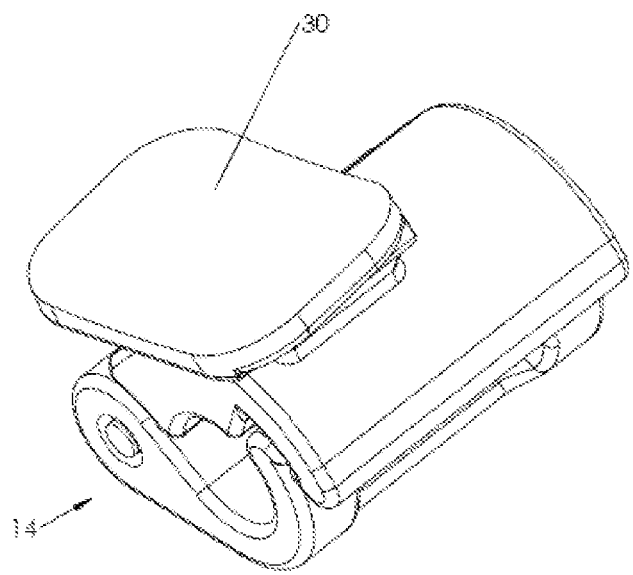
FIG. 10 is a bottom view of a mechanical locking device with a lingual bracket.

FIG. 10 is a bottom view of an embodiment of a mechanical locking device clamp 14 with a lingual bracket 30.

Figure 11:
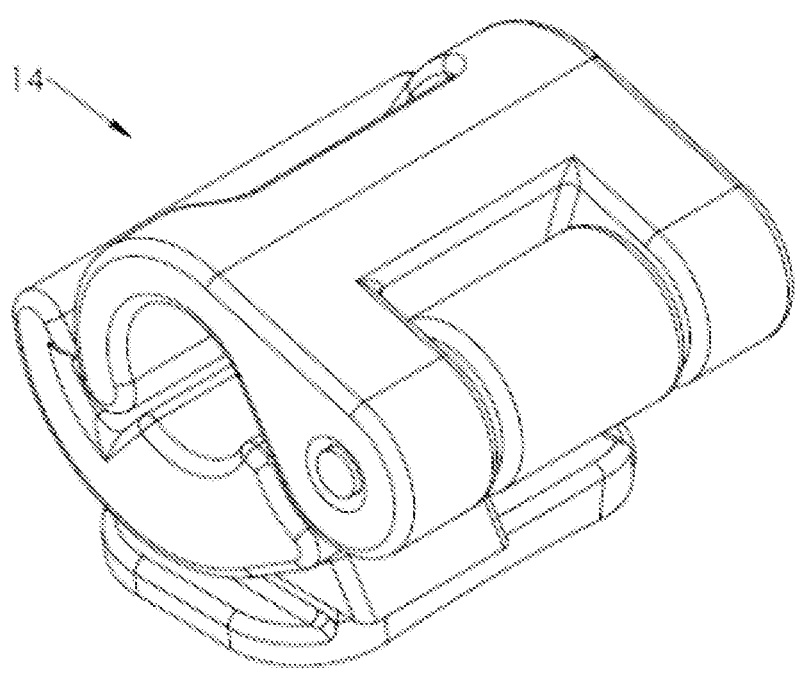
FIG. 11 is a top view of the embodiment of FIG. 10.

FIG. 11 is a top view of the embodiment of FIG. 10.

Figure 11A:
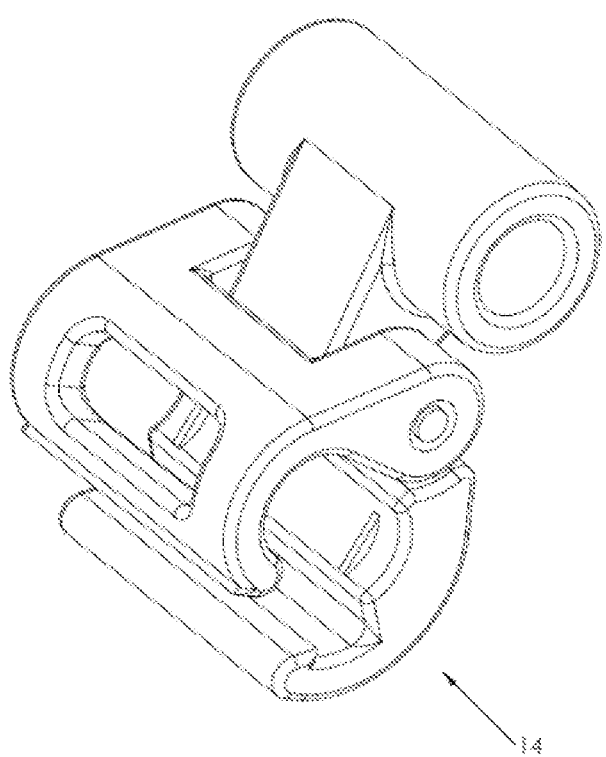
FIG. 11a is a view of a clamp with locking teeth, which bite into FFM.

FIG. 11*a* is a view of a locking device clamp 14 with locking teeth in luman.

Figure 12:
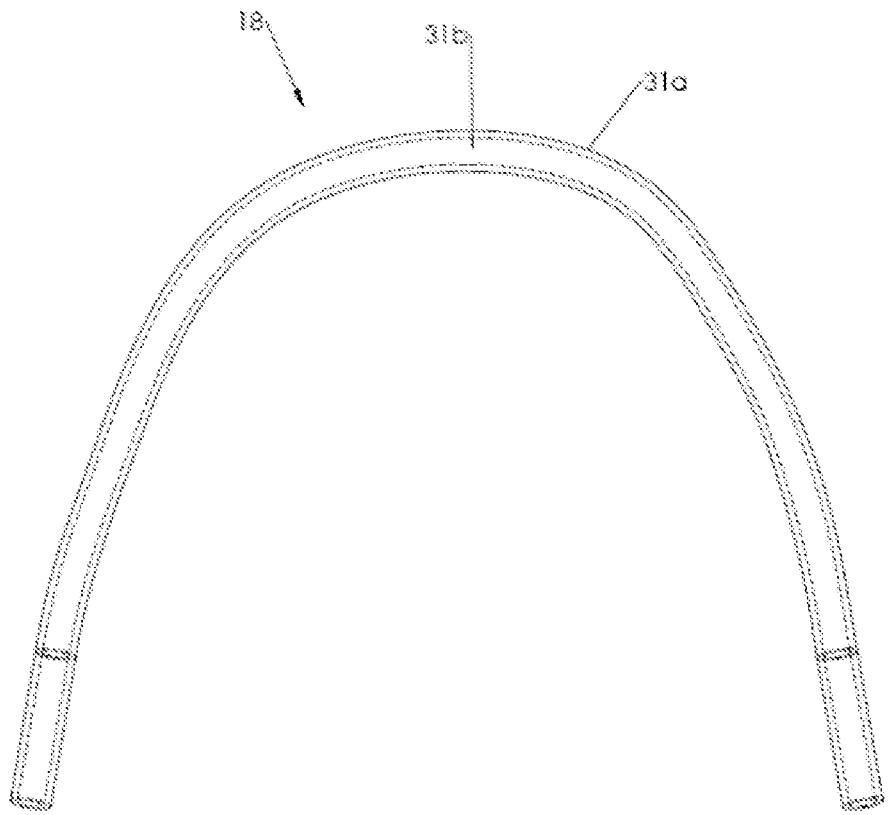
FIG. 12 is a perspective view of an uncured FFM/Flexible curable rope or Flex fit module

FIG. 12 is a perspective view of an uncured FFM 18 made of a tube 31*a* filled with a resin 31*b*, which can be chemically adjusted to achieve different physical characteristics and other relevant properties. The tube 31*a* surrounding or encasing this resin 31*b* also can be similarly modified by altering materials or width of tube 31*a* to change its physical properties for the mechanical clamping or biting into via clamp requirements.

Figure 13:
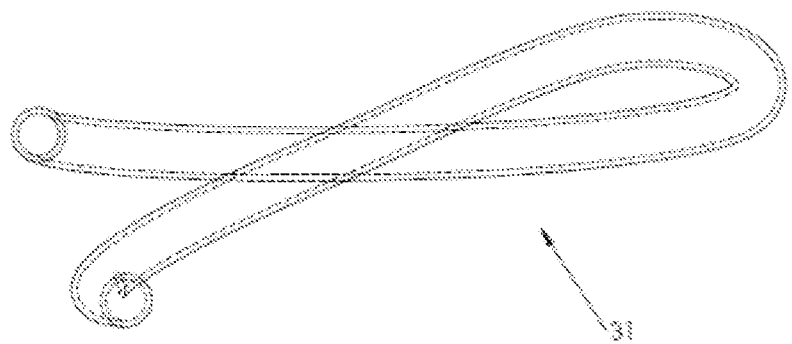
FIG. 13 is another perspective view of a randomly shaped and cured FFM of FIG. 12.

FIG. 13 is a perspective view of a cured FFM 31 of FIG. 12 placed in position.

Figure 14:
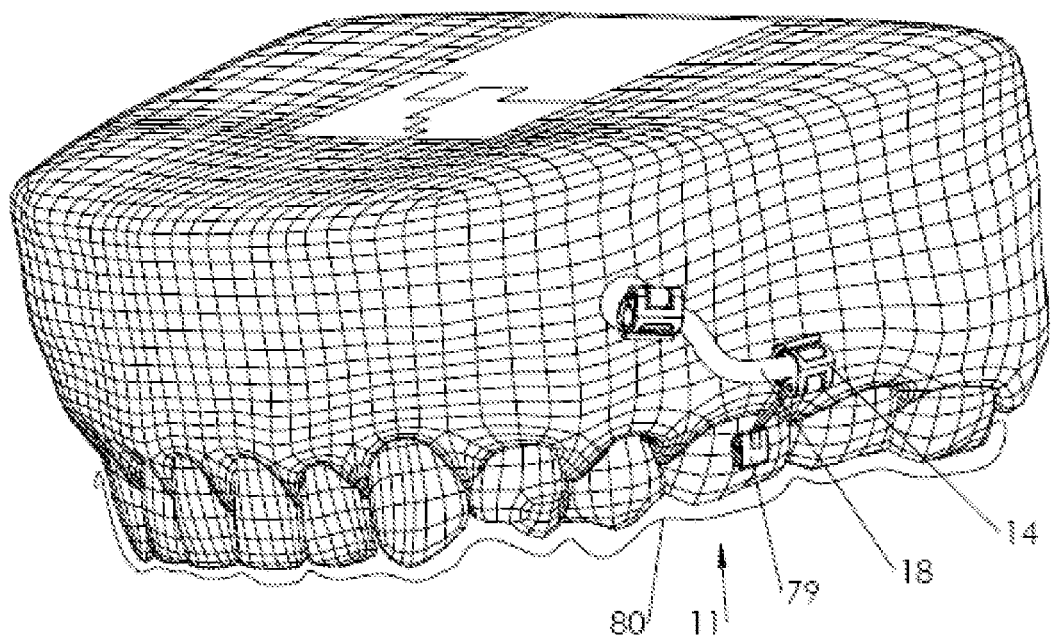
FIG. 14 is a perspective view of a bracket attached to a clamp for use with removable invisible aligners.

FIG. 14 is a perspective view of invisible removable aligner 80 adapted with the invention 10. The aligner 80 fits over tooth and bracket 79 combination easily as to not to inhibit the placement of the invisible removable aligner 80 while at the same time holding the tooth in a fixed position. The bracket 79 or bracket on band (not shown) is attached to tooth and fixed to the clamp apparatus with a solid metal connection which is part of the clamp bracket combination and is one piece. The metal portion extends past the border of the invisible removable aligner to the clamp following the anatomy of the hard and soft tissue as it becomes a clamp where it is fastened to the FFM 18. Actual bracket 79 will be larger and oval in shape than that shown in 79.

Figure 15:
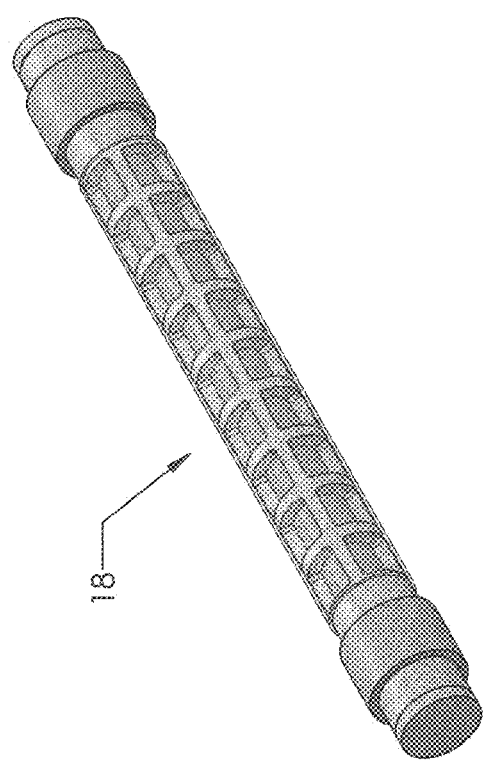
FIG. 15 is a perspective view of a composite flexible curable resin rope 18.
Figure 16:
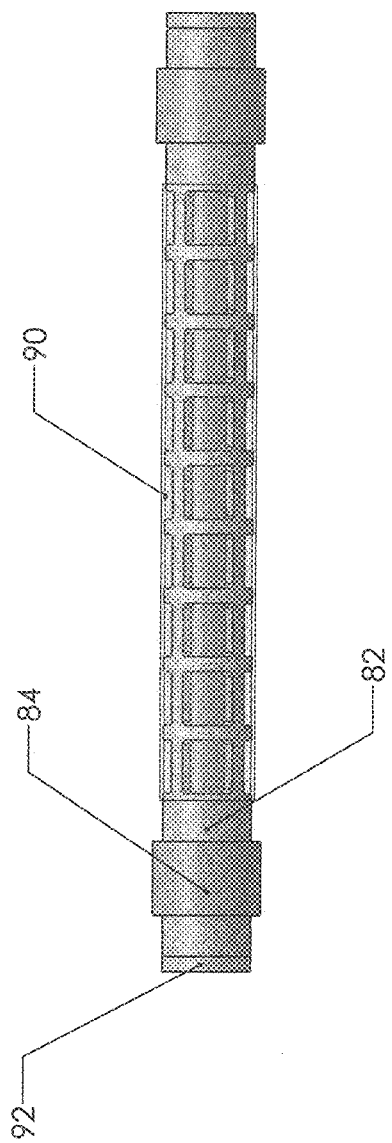
FIG. 16 is a side view of the embodiment of FIG. 15.
Figure 16A:
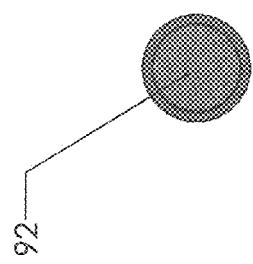
FIG. 16a is a top view of the cap of FIG. 15.

FIG. 15 is a perspective view of a composite flexible curable resin rope 18. FIG. 16 is a side view of the embodiment of FIG. 15 with a flexible structural component 82 surrounded by a ring 84 connected to the encapsulation segment 90 covered by an end cap. FIG. 16*a* is a top view of the end cap 92. The curable resin rope 18 has a flexible structural component 82 with a ring 84 connector encasing a curable resin encapsulation 92 shown in FIG. 17. The clip on band component 82 and collar ring 84 are one type of fastener, which become a fastener when combined with the clips on the bands shown in FIGS. 20 and 21, but many other different options are available, such as clamps, etc.

Figure 17:
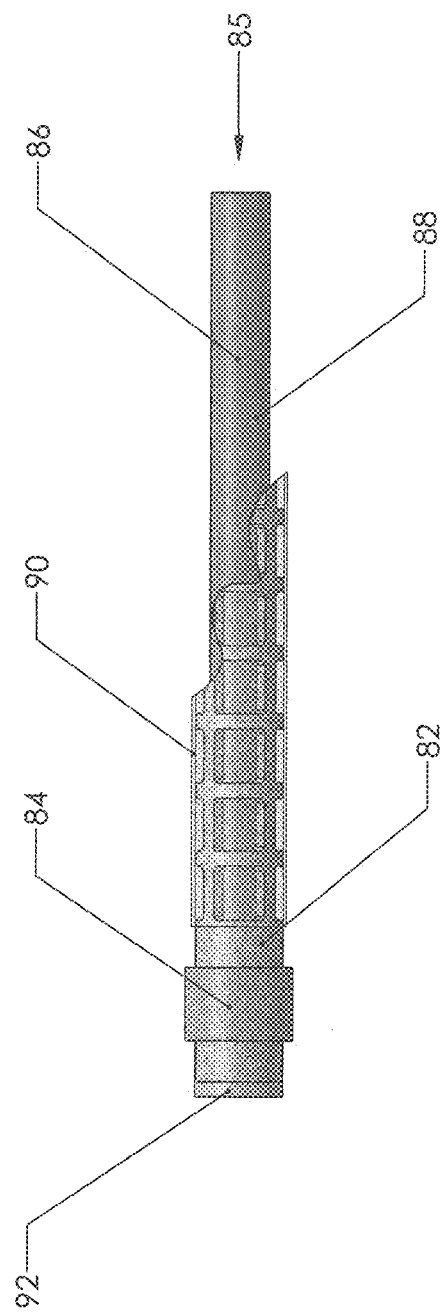
FIG. 17 is a cut-away view of the embodiment of FIG. 16.

FIG. 17 is a cut-away view of the embodiment of FIG. 16 showing the curable resin component 85 containing fibers 86 impregnated with a curable resin 88 encapsulated with an encapsulation component 90 and the structural flexible component 82. The ends of the curable resin rope 18 are covered with end caps 92 creating a rope of any shape and diameter to be manipulated into a custom position within the oral cavity where the FFM is cured to hold said position and used for orthodontic holding or movement of a tooth or teeth.

Figure 18:
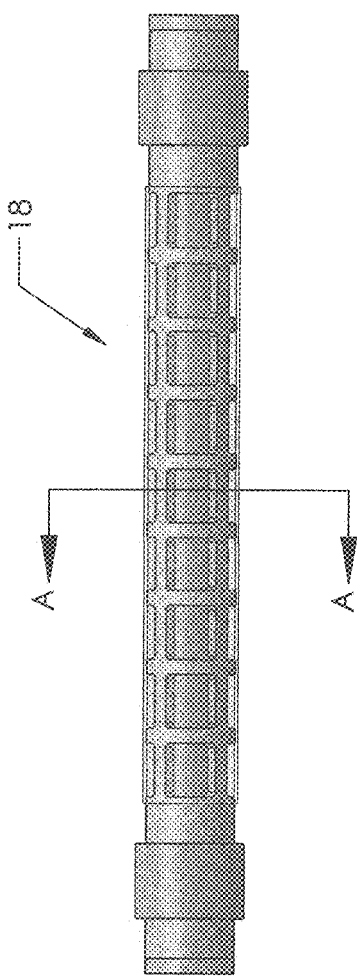
FIG. 18 shows the location of cross section AA of the curable resin rope 18 shown in FIG. 16.
Figure 19:
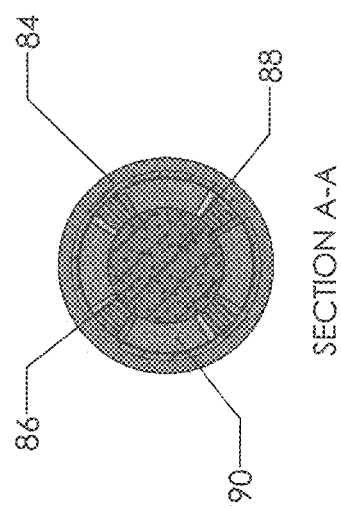
FIG. 19 is a cross section AA showing the fibers impregnated within a curable resin, the encapsulation component and the ring.

FIG. 18 shows the location of cross section AA of the curable resin rope 18 shown in FIG. 19. FIG. 19 shows the fibers 86 impregnated with a curable resin 88, the encapsulation component 90 and the ring 84.

Figure 20:
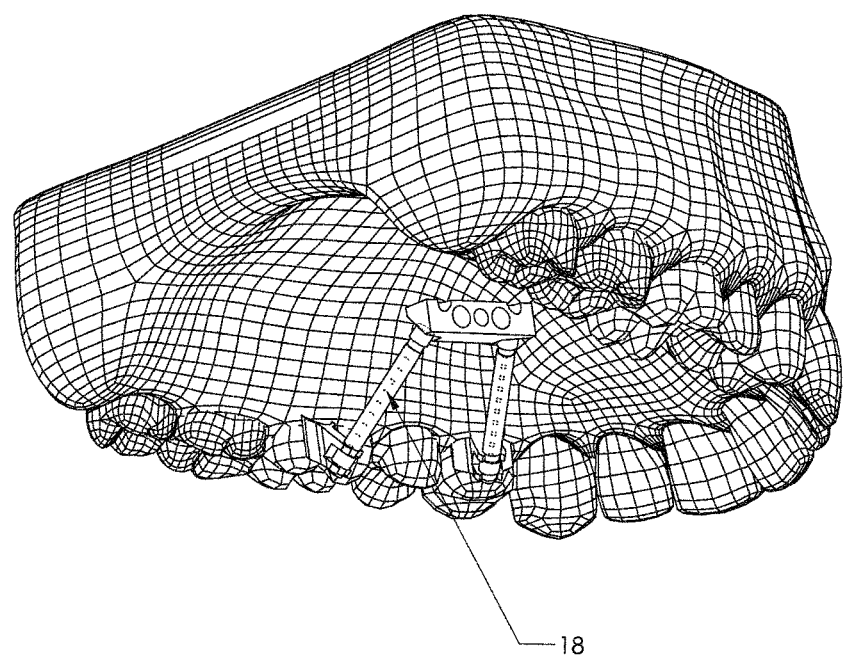
FIG. 20 illustrates two composite flexible curable resin ropes of FIG. 15 affixed to various orthodontic appliances and components.
Figure 21:
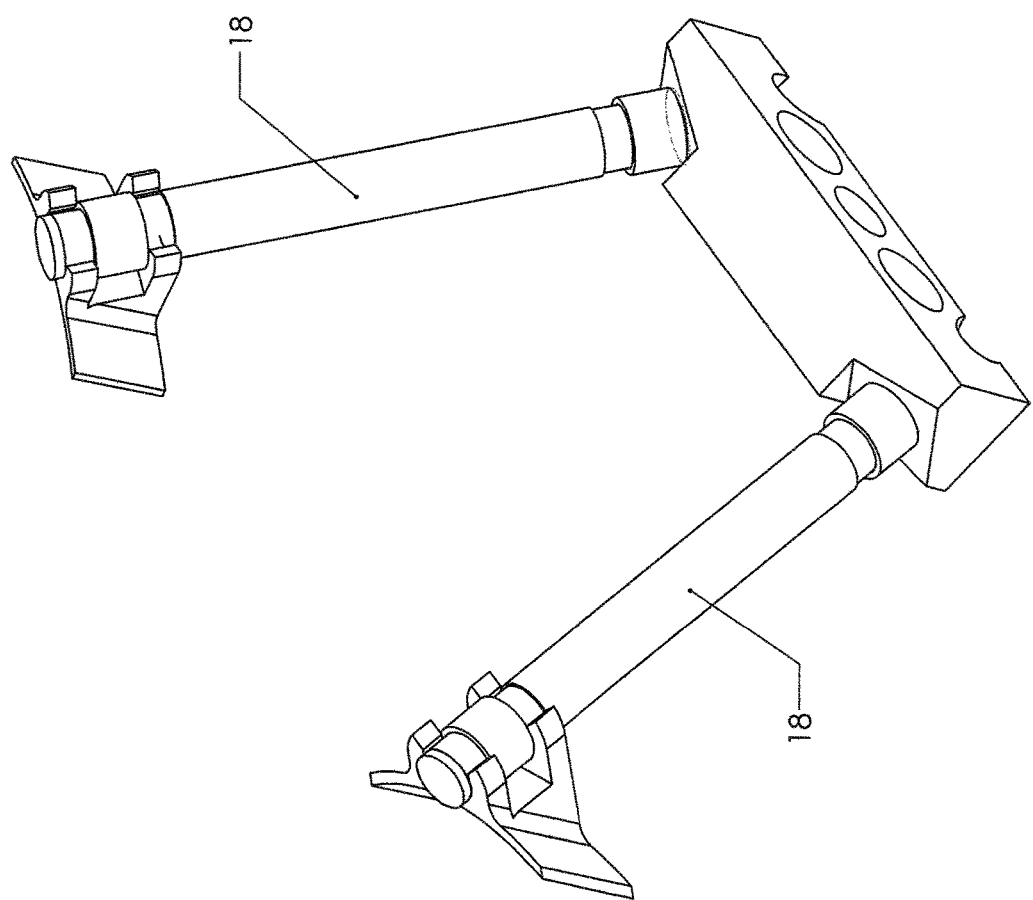
FIG. 21 is an expanded view of the construct of FIG. 20.

FIG. 20 illustrates two composite flexible curable resin ropes of FIG. 15 affixed to orthodontic appliances and components better shown in FIG. 21. This appliance can be attached to TADS 12 as is, or can be attached to a second identical contralateral half by means of an expansion screw and become a rapid palatal expander 34. It can be attached to bone or teeth or both in a custom fashion. Although the orthodontic appliances and components of FIG. 20 illustrate certain fasteners and components, they may be combined with any clips, brackets, and bands.

This invention 10 provides a new category of custom, single visit, comfortable appliances, which maintain rigid positioning of a desired leverage point or points between teeth and appliances. Biased mechanics and anchorage requirements are now easier and more predictable while patient compliance is reduced. Because the orthodontist can custom place his appliance exactly where he needs it the orthodontic mechanics of tooth pulling, pushing, tipping, rotating, extruding, intruding and bodily movement and alignment are simplified.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

I claim:

1. An Orthodontic system comprising:
  a. at least one uncured moldable Flex Fit Module or flexible resin rope(s) (FFM) consisting of a flexible curable resin material without a tube surrounding the resin material, wherein each Flex Fit Module or flexible resin rope(s) (FFM) has a diameter and length selected to apply required orthodontic biasing forces to obtain selective movement of teeth, which are moldable when in use and are custom aligned and shaped and positioned within a patient's oral cavity along desired segments of teeth, gums, palate and buccal and lingual portions in both the mandible and maxilla with physical properties including slump, firmness, wetness, malleability, flexibility, strength, hardness, flowability, and curability to temporarily hold the Flex Fit Module or flexible resin rope(s) (FFM) in a fixed position until cured with heat, time, chemical or light curing with no flexible structural components outside of the FFM itself, and when in use in a cured state forms a rigid structure capable of withstanding and directing the orthodontic biasing forces with exact placement;

b. at least one first anchorage element selected from the group comprising temporary anchorage device(s) (TAD) or tooth positioning orthodontic appliance(s);

c. at least one second anchorage element selected from the group comprising temporary anchorage device(s) (TAD) or tooth positioning orthodontic appliance(s); wherein each of said anchorage elements(s) is provided with anchorage structure and a fastener which connects components of the orthodontic system; said anchorage structure adapted to secure to a tooth, teeth, oral structure(s), orthodontic appliance(s), arch-wires, or orthodontic hardware within a patient's oral cavity to provide an anchoring point, and said fastener is adapted to secure said Flex Fit Module or flexible resin rope(s) (FFM).

2. The Orthodontic system according to claim 1, wherein the curable resin material contains anionic, cationic, or free radical polymers selected from the group consisting of at least one of the following: 2,6-Di-tert-butyle-4-methylphenol, Bisphenol A ethoxylate dimethacrylate, PEG 400 Extended Urethane dimethacrylate, Aliphatic Urethane Acrylate, Urethane dimethacrylate, Diurethane dimethacrylate isomers mixtures, Ethyl 4-(dimethlyamineo) benzoate, epoxies, acrylates, cyanoacrylates, silicones, polyurethanes, polyureas, oligomer acrylates, Triethylene glycol dimethacrylate, urethane methacrylate oligomers, low molecular weight trimethacrylates or other polyethylene glycol (PEG) monomers, Bisphenol A glycerolate dimethacrylate, oligomers, monomers, polymers, cyanoacrylates, elastomers, polyolefins, acrylics, plastics, silicone and photo initiators.

3. The Orthodontic system according to claim 1, wherein the first anchorage elements are adapted to be fastened or connected to the Flex Fit Module or flexible resin rope(s) (FFM) comprise at least one of the following: a temporary anchorage device (TAD), bone plates, orthodontic hardware, removable orthodontic appliances, fixed orthodontic appliances, space maintenance appliances, orthodontic braces, ligatures, clear removable aligners, a second Flex Fit Module or flexible resin rope(s) (FFM), a flex fit wafer (FFW), band(s), bracket(s), custom milled, injection molded, or additively manufactured brackets or bands, mesh pads, tubes, wires, orthodontic auxiliaries, hooks, buttons, elastics, elastomerics, inter-oral and extra-oral orthodontic appliances, active tooth positioning orthodontic appliance(s), magnets, visible and non visible light emitting appliances, vibration devices, or orthodontic appliances which deliver an electrical current(s) into the oral structures.

4. The Orthodontic system according to claim 1, wherein the second anchorage elements are adapted to be fastened or connected at any point along the Flex Fit Module or flexible resin rope(s) (FFM) and comprise at least one of the following: a temporary anchorage device (TAD), bone plates, orthodontic hardware, removable orthodontic appliances, fixed orthodontic appliances, space maintenance appliances, orthodontic braces, ligatures, clear removable aligners, a second Flex Fit Module or flexible resin rope(s) (FFM), a flex fit wafer, band(s), bracket(s), custom milled, injection molded, or additively manufactured brackets or bands, mesh pads, tubes, wires, orthodontic auxiliaries, hooks, buttons, elastics, elastomerics, inter-oral or extra-oral orthodontic appliances, active tooth positioning orthodontic appliance(s), magnets, visible and non visible light emitting appliances, vibration devices, or orthodontic appliance(s) which deliver an electrical current(s) into the oral structures.

\* \* \* \* \*